(12) United States Patent
Back (10) Patent No.: US 10,126,280 B2
(45) Date of Patent: Nov. 13, 2018

(54) DEVICE AND METHOD FOR TESTING UNDERGROUND ARGON

(71) Applicant: The Trustees of Princeton University, Office of Technology and Trademark Licensing, Princeton, NJ (US)

(72) Inventor: Henning Back, Woodridge, IL (US)

(73) Assignee: The Trustees of Princeton University, Office of Technology and Trademark Licensing, Princeton, NJ (US)

( * ) Notice: Subject to any disclaimer, the term of this patent is extended or adjusted under 35 U.S.C. 154(b) by 520 days.

(21) Appl. No.: 14/880,345

(22) Filed: Oct. 12, 2015

(65) Prior Publication Data

US 2016/0109418 A1    Apr. 21, 2016

Related U.S. Application Data (60) Provisional application No. 62/065,341, filed on Oct. 17, 2014, provisional application No. 62/115,723, filed on Feb. 13, 2015.

(51) Int. Cl.
  *G01N 33/00*  (2006.01)
(52) U.S. Cl.
  CPC ................. *G01N 33/0004* (2013.01)
(58) Field of Classification Search
  CPC .................................. G01N 33/0004
  USPC ........................................ 73/23.36
  See application file for complete search history.

(56) References Cited

U.S. PATENT DOCUMENTS

| | | | |
|---|---|---|---|
| 4,757,203 A * | 7/1988 | Gil | B01D 59/44 250/281 |
| 5,161,380 A | 11/1992 | Cheung | |
| 5,714,678 A * | 2/1998 | Jurcik | G01N 33/0004 73/23.2 |
| 5,916,261 A | 6/1999 | Bonaquist et al. | |
| 6,574,988 B1 | 6/2003 | Saulnier et al. | |
| 2008/0221798 A1* | 9/2008 | Pariag | G01V 9/00 702/9 |

(Continued)

OTHER PUBLICATIONS

Henning O. Back. "DarkSide and its Low Radioactivity Argon Target." FCPA Seminar, Feb. 22, 2012, Princeton University. 51 pgs.

(Continued)

*Primary Examiner* — Jennifer Simmons
(74) *Attorney, Agent, or Firm* — Moser Taboada (57) ABSTRACT

Provided among other things is a method of conducting on-site quality control during production of underground argon, comprising: (1) concurrent with extraction of underground argon material, periodically sampling the argon material; (2) measuring an index amount of at least one of (a) an $^{36}$Ar to $^{40}$Ar ratio or (b) an $^{38}$Ar to $^{40}$Ar ratio from the sampled argon material; and (3) conducting one or more of the following: (a) interrupting production to determine a source of infiltration when a measured index amount for a sample indicates an infiltration of atmospheric argon that is outside a production quality standard, or (b) cataloging whether a production run satisfies a product quality standard for lack of atmospheric argon based on the measured index amounts for the samples when a production run for the argon is complete.

20 Claims, 3 Drawing Sheets

(56) References Cited

U.S. PATENT DOCUMENTS

| | | | |
|---|---|---|---|
| 2009/0114809 A1* | 5/2009 | Hotchkis | B01D 59/44 |
| | | | 250/282 |
| 2015/0000374 A1* | 1/2015 | Romanak | G01M 3/226 |
| | | | 73/23.35 |

OTHER PUBLICATIONS

Aalseth et al. "Measurement of $^{37}$Ar to Support Technology for On-site Inspection under the Comprehensive Nuclear-Test-Ban Treaty." Pacific Northwest National Laboratory. 2010. 5 pgs.

Aalseth et al. "$^{37}$Ar Background Measurements Supporting On-Site Inspection." Pacific Northwest National Laboratory. U.S. Department of Energy. 1 pg.

Geller et al. "Thermoacoustic Enrichment of the Isotopes of Neon." Acoustical Society of America, vol. 115 No. 5, Pt. 1. May 2004. p. 2059-2070.

Back et al. "First Commissioning of a Cryogenic Distillation Column for Low Radioactivity Underground Argon." DarkSide Collaboration. arXiv:1204.6061v2 [astro-ph.IM] May 2012. 5 pgs.

Back et al. "First Large Scale Production of Low Radioactivity Argon from Underground Sources." DarkSide Collaboration. arXiv:1204.6024v2 [astro-ph.IM] May 2012. 5 pgs.

* cited by examiner

DEVICE AND METHOD FOR TESTING UNDERGROUND ARGON

CROSS-REFERENCES

This application claims the priority of U.S. application Ser. No. 62/065,341, filed Oct. 17, 2015, and U.S. application Ser. No. 62/115,723, filed Feb. 13, 2015, the contents of which are incorporated herein in their entirety.

GOVERNMENT INTEREST

This invention was made with government support under Grant No. PHY-1242585 awarded by the National Science Foundation. The government has certain rights in the invention.

FIELD

The present application relates generally to methods and devices for confirming the underground source of argon.

BACKGROUND

There is a growing marketplace for argon gases and liquids with little to no radioactive content from Argon-39 ($^{39}$Ar). Argon gas is generally collected from the atmosphere. However, atmospheric argon contains a small amount of $^{39}$Ar and is, therefore, radioactive. This radioactivity which is typically found in atmospheric argon is in low amount but interferes with uses of argon, such as, for example, in dark matter detectors, and in proportional counters used to search for $^{37}$Ar (a marker for nuclear test ban violations).

Argon gas that is collected from sources deep underground has been found to not contain $^{39}$Ar and, therefore, is not radioactive. Specifically, $^{39}$Ar in the atmosphere is derived from the interaction of $^{40}$Ar with cosmic rays. As such, $^{39}$Ar is much less in underground sources that are protected from cosmic rays. However, in producing underground argon, one must take care that there is not an infiltration of too much (or any) atmospheric argon. The infiltration could be from a longer term geologic phenomenon, or associated with the production process. Thus, it would be useful to have a simple, rapid test to exclude the possibility of atmospheric Argon during production. However, direct testing for $^{39}$Ar is a lengthy process, and thereby does not lend itself to a production-level test.

The difficulty of measuring $Ar^{39}$ is difficult to overstate. In the atmosphere the $Ar^{39}$ to $Ar^{40}$ ratio is $10^{\wedge}$-15. The only way to measure the $Ar^{39}$ directly is to build a multi million dollar ultra sensitive radiation detector. Applicant knows of only 2 published efforts to measure $Ar^{39}$ in underground argon. Method one measured the scintillation light from 1 kilogram of liquefied argon, and measured it for a month or more, and then did not directly succeed. The conclusion was that the researchers did not see it. The other measurement used 157 kg of the underground $Ar^{39}$ (the world's supply). This was an international collaborative effort involving on the order of 50 scientists.

The current inventor recognized the need for a more rapid test than is available for $^{39}$Ar content, and that the ratio of $^{36}$Ar to $^{40}$Ar provides a useful surrogate test. In the atmosphere, the portion of Argon that is $^{36}$Ar is substantially higher than in underground Argon. Similarly, the ratio of $^{38}$Ar to $^{40}$Ar provides another useful surrogate test.

SUMMARY

Provided among other things is a method of conducting on-site quality control during production of underground argon, comprising: (1) concurrent with extraction of underground argon material, periodically sampling the argon material; (2) measuring an index amount of at least one of (a) an $^{36}$Ar to $^{40}$Ar ratio or (b) an $^{38}$Ar to $^{40}$Ar ratio from the sampled argon material; and (3) conducting one or more of the following: (a) interrupting production to determine a source of infiltration when a measured index amount for a sample indicates an infiltration of atmospheric argon that is outside a production quality standard, or (b) cataloging whether a production run satisfies a product quality standard for lack of atmospheric argon based on the measured index amounts for the samples when a production run for the argon is complete. In embodiments, the measuring is conducted with sufficient sampling and immediacy of timing such that any infiltration of atmospheric argon is stopped prior to being sufficient to put a production run at risk of not meeting the product quality standard, and wherein the production is conducted until a production run meeting the product quality standard is achieved.

Further provided is a system for determining whether underground-sourced argon is sufficiently free of atmospheric argon comprising: (A) an analyzer configured to provide data sufficient to determine an index amount, wherein the index amount is one of (a) an $^{36}$Ar concentration or an $^{36}$Ar to $^{40}$Ar ratio or (b) an $^{38}$Ar concentration or an $^{38}$Ar to $^{40}$Ar ratio; (B) a processor programmed to determine the determine the index amount; and (C) an indicator that receives from the processor a signal sufficient for the indicator to indicate whether the index amount meets a quality standard.

DESCRIPTION OF THE DRAWINGS

So that the manner in which the above recited features of the present invention can be understood in detail, a more particular description of embodiments of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

Figure 1:
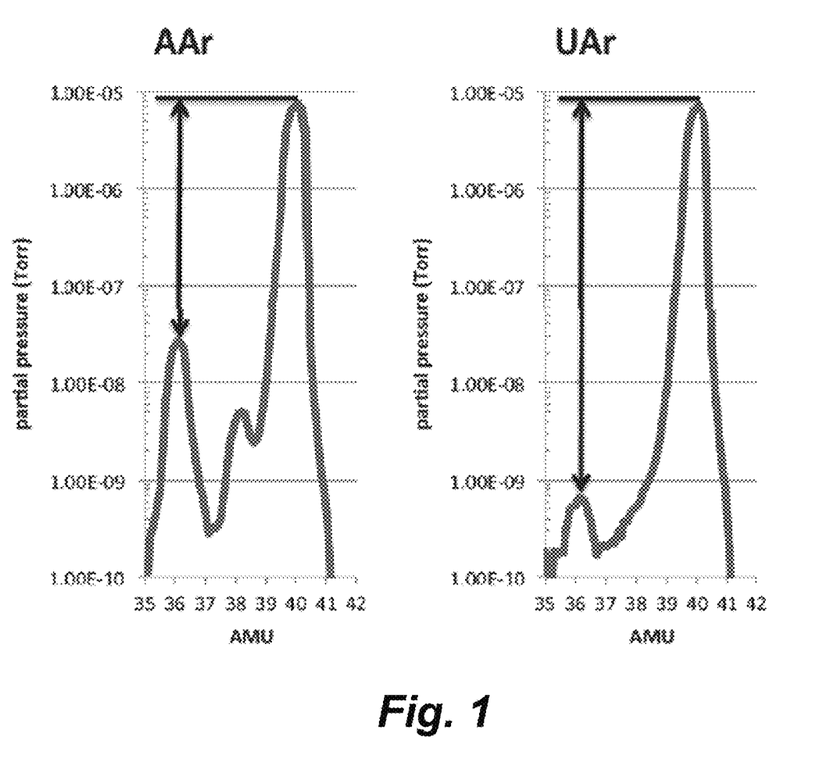
FIG. 1 shows the peaks from a gas analyzer for $^{36}$Ar and $^{40}$Ar in accordance with embodiments of the invention.

FIG. 1 shows the peaks from a gas analyzer for $^{36}$Ar and $^{40}$Ar in atmospheric argon (panel AAr) and underground argon (panel UAr, gas from Cortez, Colo.). The ratio of $^{36}$Ar to $^{40}$Ar is $3.4\times10^{-3}$ for atmospheric, and $8.9\times10^{-5}$ for underground. Thus, the ratio is 38.2 times higher in atmospheric gas. The peak for $^{38}$Ar can be seen in the atmospheric trace. While not relevant in the exemplified measurement, if the amount of $^{36}$Ar (or $^{38}$Ar) in the underground product were too low to measure, this data can still be sufficient for the detection methods described herein if the amount in the atmosphere, and the rated sensitivity of the analyzer, were enough to imply that at least a target ratio is obtained.

Testing is performed substantially continuously during production. For example, sampling frequency can be about 0.2, 0.5, 1 or 3 per min or higher. For each production container, the record for this ratio during production can be associated in the records, or a condensed form such as an average can be associated. The ratio for the bulk production container can also be measured, and associated in production records. Thus, if any production containers that prove to have a higher than optimum amount of radioactivity or directly measured $^{39}$Ar, then the associated record can be used to tighten as needed production standards.

As exemplified above, $^{39}$Ar is low in underground argon. The $^{36}$Ar to $^{40}$Ar ratio (or $^{38}$Ar to $^{40}$Ar ratio) can vary with the geology. For example, mantle argon, which can be sampled at mid-ocean ridges, can have a $^{36}$Ar to $^{40}$Ar ratio that is still lower than for argon sources from the earth's crust. Thus, the production ratio sought to be maintained at a given production site will vary. Longer-term testing can establish the suitability of a production site, such that the ratio, as determined for the site, can then be used to provide quality control during production. End users can use the test provided by embodiments of the invention to confirm quality upon or after delivery.

The gas isotope analyzer used in the method can, for example, utilize mass spectroscopy ("MS"). For example, any MS device can be used that is operable with gases and has sufficient resolution such that a ratio difference between atmospheric and underground can be detected sufficient to meet production standards. In most cases, a ratio difference of about 20-fold or more is detected, such as about 30-fold or more, or 35-fold or more.

In embodiments, the resolution and sensitivity of the gas isotope analyzer is sufficient to detect a ratio of $^{36}$Ar to $^{40}$Ar (or $^{38}$Ar to $^{40}$Ar) that, based on historical experience, corresponds for a given production site to a mole fraction of $^{39}$Ar suitable for use for example in a detector, such as a ratio to total argon of less than about $8.1\times10^{-16}$.

In practice, given the difficulty in measuring $^{39}$Ar, the production standard for the ratio ($^{36}$Ar to $^{40}$Ar or $^{38}$Ar to $^{40}$Ar) can be based on the ratio being determined with pilot production runs where air infiltrations are carefully excluded. If there are outlier high ratios, these will indicate when infiltrations have occurred, and help validate the lower ratio of other runs. Of course, the geology of the production site will be considered to help avoid more systematic infiltrations. Moreover, the ratio data described herein will help validate an appropriate ratio at another site.

Argon has three primary stable isotopes, $^{36}$Ar, $^{38}$Ar and $^{40}$Ar. These are found in all Argon at fixed fractions. In the atmosphere their relative abundances are very well understood with 40Ar=99.6035% of argon (mole fraction), $^{36}$Ar=0.3336%, and $^{38}$Ar=0.0629%. In underground argon, the fractions of these isotopes differ from those of the atmosphere An exemplary embodiment employs a commercially available real-time gas analyzer, such as a Universal Gas Analyzer (UGA, employing a quadrupole MS) from Stanford Research Systems (thinksrs.com). The gas analyzer may need calibration or adaptation appropriate for measuring the levels of $^{36}$Ar and $^{40}$Ar or $^{38}$Ar and $^{40}$Ar. A processor can be configured to receive the data stream and programmed to determine and compare the ratios described above. A monitoring device can include an indicator, such as a display, configured to provide an indication that there has been contamination with atmospheric argon, such as if the compared ratios differ and/or the data provides an indication of contamination.

The exemplary UGA analyzer has a resolution of <0.5 amu at 10% of peak height, and a detection limit <10 ppm with Faraday cup detector or <1 ppm with electron multiplier. In embodiments, the resolution is about ≤1 amu at 10% of peak height (namely, such that two equal peaks separated by 1 amu will have overlap at no more than 10% of peak height. In embodiments, the detection limit will be about ≤20 ppm.

Should the ratio prove higher than ideal for a production run, it may be that the ratio still fits within production standards. Or, the production run may meet standards for a lesser purity product. For example, it might not be suitable for use in a dark matter detector, but still meet the needs of a less exacting use of low radioactivity argon.

The disclosed approach may be employed by any company that extracts and/or purifies Argon as it provides a quality assurance test and measures the possible contamination from radioactive atmospheric Argon. The disclosed approach may be employed alongside other extraction processes, e.g., the extraction of helium from carbon dioxide gas wells as it is straightforward to extract argon if one is already extracting helium.

Argon is typically separated from other gases by cryogenic fractional distillation. These methods are well developed, as exemplified by U.S. Pat. Nos. 6,574,988, 5,916,261 and 5,161,30, herein incorporated by reference in their entireties.

Embodiments consistent with the present invention relate to measuring the "index amount," which is (a) an $^{36}$Ar to $^{40}$Ar ratio or (b) an $^{38}$Ar to $^{40}$Ar ratio. In embodiments, the index amount is (a). In use for example at a well site production, it may be that the amount of $^{40}$Ar does not vary enough to need the corrective effect of expressly measuring the ratio to $^{40}$Ar. In which case, it may be appropriate to measure the concentration of $^{36}$Ar or $^{38}$Ar, or a useful, reasonably accurate, surrogate therefore. Implicitly, such a measurement measures the corresponding ratio. For best accuracy, the ratio is explicitly measured. The express ratio can for example be more important for the documentation of the pooled product of a production run. However, when historical consistency in the $^{40}$Ar number allows, then the concentration of $^{36}$Ar or $^{38}$Ar may be the focus for example of real time measurement (though in fact the ratio is implicit). In for example real time measurements the peak height corresponding to $^{36}$Ar or $^{38}$Ar can provide a good approximation of concentration, thereby in appropriate circumstances providing the index amount.

Note that the concentration may not be expressly named in the output of the method, but it is implicit. (E.g., amount per amount of material sampled.)

In embodiments of the invention, sampling of argon material is "concurrent" with extraction if samples are taken anywhere in the processing stream, from the initial extraction to the conduit that takes purified argon to its collection tank. It is believed to be such that monitoring can be conducted at any such point in the process. However, measurements taken with higher concentrations of argon are preferred, since the $^{36}$Ar or $^{38}$Ar concentration will be higher, such that it can be more accurately measured.

"Underground argon material" is any material extracted from the ground for processing to underground argon, and any of the process streams in the purification process for the original extracted material. While the argon of interest is gas at standard temperature and pressure (STP), at various stages of processing it and its contaminants may be gas or liquid (or in the case of some contaminants, solid).

Sampling and measuring are conducted in "real time" if the measured results for at least one sample is obtained prior to the end of a production run, and systems are in place such that all samples can be measured in about the time needed such that early samples can be read prior to the end of a production run.

A "production run" is an amount of collected argon for which the manufacturer intends to provide a production run identifier and associate quality control documentation.

Quality control data is "cataloged" with a production run if it is stored in hard or electronic form such that it can be called up by the production company with respect to the production run. The data may be sent with shipments from the production run, or held by the production company in case of need.

A "production quality standard" is based on the index amount and is for data generated during the production process, not data from the aggregate product. If a production quality standard is breached, the degree of breach may determine whether a product quality standard will be breached if production is interrupted, then restarted after repair (e.g., trouble-shooting for a source of infiltration).

A "product quality standard" is based on the index amount and is for data generated from the aggregate product.

Figure 2:
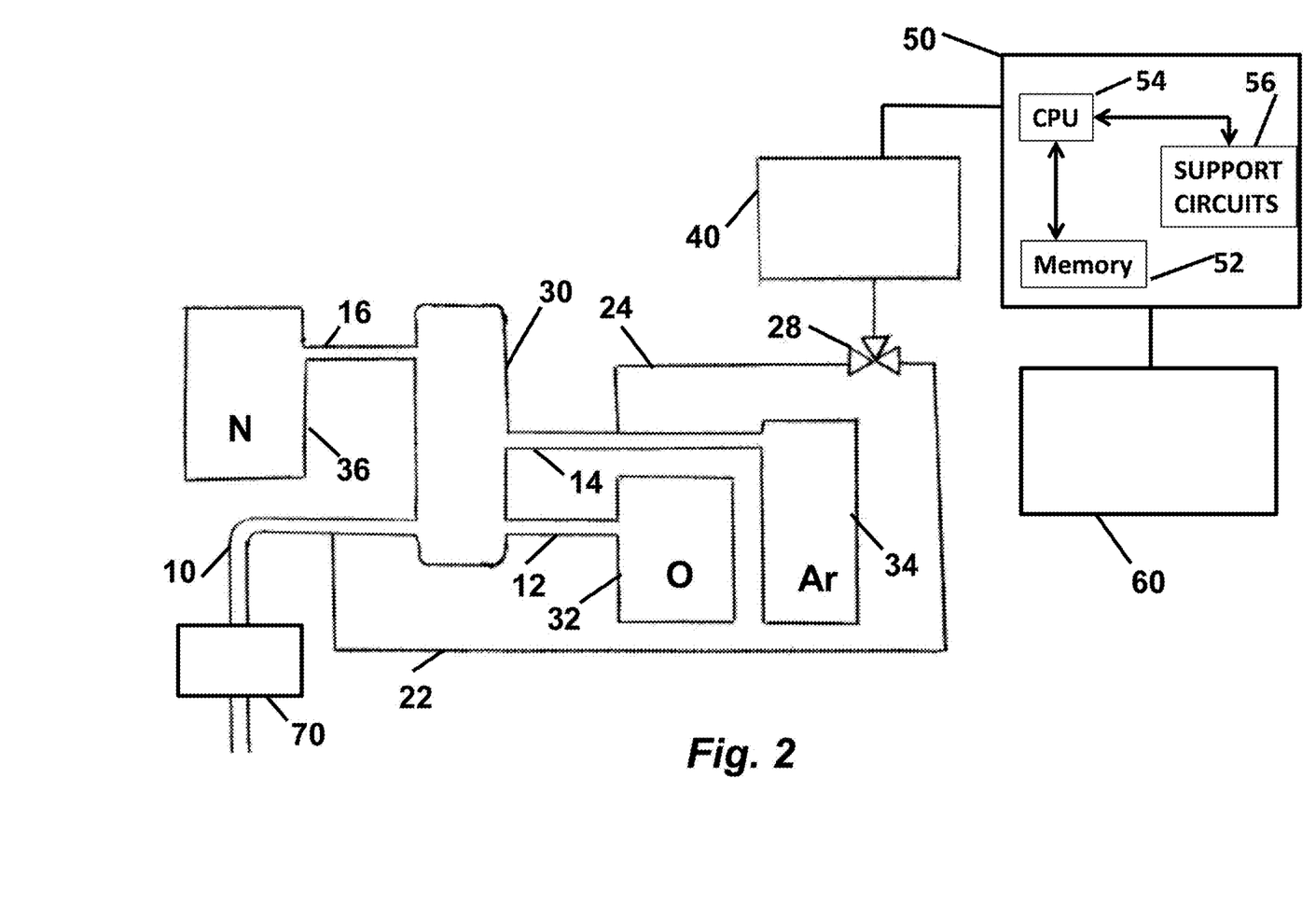
FIG. 2 is a schematic of a system for determining if underground-sourced argon is sufficiently free of atmospheric argon in accordance with embodiments of the invention.

FIG. 2 shows an illustrative schematic of a system for determining if underground-sourced argon is sufficiently free of atmospheric argon. Conduit 10 brings in underground argon material, for example from a wellhead, to a separation device 30 (e.g., cryogenic distillation device, which can have several separation stages). While not shown, conduit 10 can pass the underground argon material through preliminary processing system(s) 70, such as for example a Vacuum Pressure Swing Adsorption (VPSA) system. Such preliminary processing can include steps or systems to separate $CO_2$, and other gases.

VPSA systems exploit the different rates of adsorption of different species at a partial pressure. For example, zeolite NaX can be selected as the adsorbent for a VPSA stage (e.g., first stage), given its very high selectivity for CO2 over argon. This stage can absorb for example $CO_2$, $CH_4$ and other hydrocarbons, and $H_2O$, substantially increasing argon concentration. For example, Li-LSX, a lithium-exchanged, low silicate 13X zeolite with selectivity for nitrogen, be selected as the adsorbent for a VPSA stage (e.g., second stage). If the source gas has helium, this may be concentrated along with argon by the VPSA systems.

Output from the separation device can be conduits 12, 14 and 16, which direct for example oxygen to container 32, argon for example to container 34, and nitrogen for example to container 36. Helium can be passed for example through a waste outlet (not shown). Sampling conduits 22 and 24 can direct sample amounts of material to gas analyzer 40, for example via three-way valve 28 (which can be automated, for example under the control of controller 50). Gas analyzer 40 incorporates or operates in conjunction with controller 50. Controller 50 can send an indication of whether the material is sufficiently free of atmospheric argon to indicator 60.

In any aspect that calls for a controller or computer, the devices consistent with the present invention can have a controller 50 such as in FIG. 2, which can comprise a central processing unit (CPU) 54, a memory 52, and support circuits 56 for the CPU 754 and is coupled to and controls the analyzer or, alternatively, operates to do so in conjunction with computers (or controllers) connected to the analyzer. For example, another electronic device can supply software, or operations may be calculated off-site with controller 50 coordinating off-sight computer operations with the local environment. The controller 50 may be one of any form of general-purpose computer processor, or an array of processors, that can be used for controlling various devices and sub-processors. The memory, or computer-readable medium, 52 of the CPU 54 may be one or more of readily available memory such as random access memory (RAM), read only memory (ROM), flash memory, floppy disk, hard disk, or any other form of digital storage, local or remote. The support circuits 56 are coupled to the CPU 54 for supporting the processor in a conventional manner. These circuits can include cache, power supplies, clock circuits, input/output circuitry and subsystems, and the like. Methods of operating the analyzer may be stored in the memory 752 as software routine that may be executed or invoked to control the operation of the devices. The software routine may also be stored and/or executed by a second CPU (not shown) that is remotely located from the hardware being controlled by the CPU 754. While the discussion in this patent application may speak of the "controller" taking certain actions, it will be recognized that it may take such action in conjunction with connected devices.

Indicator 60 can be a display, a chart recorder, an electronic file, or the like.

Figure 3:
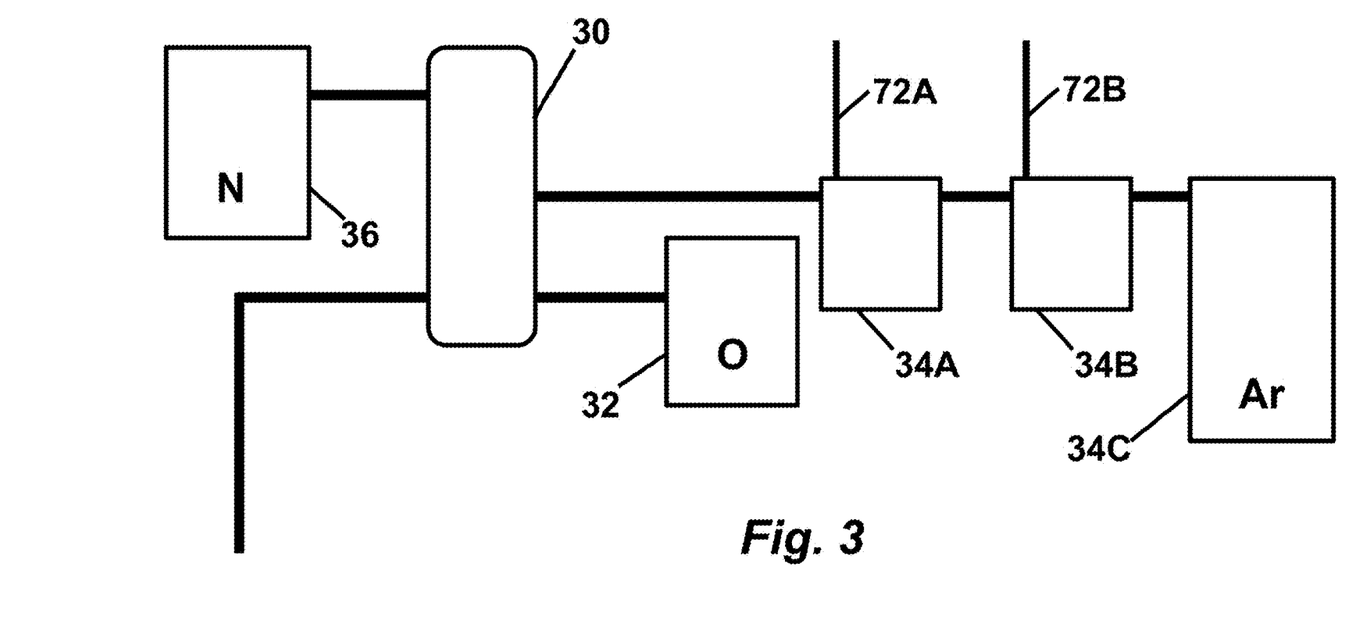
FIG. 3 is a schematic of a system for determining if underground-sourced argon is sufficiently free of atmospheric argon in accordance with embodiments of the invention.

FIG. 3 is a schematic of a system (simplified from FIG. 2) that includes one or more reservoirs (34A, 34B) of nominally purified argon. If the analyzer (not shown here) provides data indicating an infiltration of atmospheric argon, the reservoirs are sized in view of the frequency of testing results, such that all argon with a questionable index amount can be diverted from proceeding to reservoir 34C. For example, the argon can be vented (e.g., vents 72A, 72B), or directed to a reservoir for lower quality argon. Diversion can be automated under the control of controller 50 and the index amount data. If there is more than one such reservoir, the controller can take into account the size of the infiltration, and the timing of the data on the infiltration, to determine which reservoirs to divert.

In the production that has been conducted in Cortez, Colorado, argon was collected from a stream of gas from a $CO_2$ well with a Vacuum Pressure Swing Adsorption (VPSA) plant. The extracted gas contains argon at 400-600 ppm, and the VPSA plant produced an output stream with an argon concentration of 30,000-50,000 ppm (3-5%) in a single pass. This gas was further processed by cryogenic distillation. The argon production rate was presently 0.5 kg/day. Back et al., rXiv:1204.6024 [astro-ph.IM] (2012).

The distillation column accepted a mixture of argon, helium, and nitrogen and returned argon with low nitrogen contamination, such as less than 10 ppm. In continuous mode the distillation column produced argon at 99.9% purity. In batch mode, the argon purity could be increased, such as to 99.95%, with less than 300 ppm of nitrogen remaining. Collection efficiency was between 70% and 81%, at an production rate of 0.84-0.98 kg argon per day. Back et al., arXiv:1204.6061 [astro-ph.IM] (2012).

Gas analyzers will typically come with software for integrating the output peaks to associate an amount with each peak. Otherwise, such software is available from for example the suppliers of mass spectrometers. As the argon isotopes are chemically identical, they will have identical responses to the detection process (e.g., current from ionization). The software will typically include a process for deconvolution of overlapping peaks. The software may include options for the process of deconvolution. The specific type of peak quantitation software is not important as long as it is generally recognized as providing values that are reasonable and reasonably reproducible. More important is that the methods used for production testing are the same as used in the calibration processes that determined production or product quality standards.

The controller will compute the ratio or concentration. If the amount is outside of a quality standard, that might be apparent in the Indicator 60 by the controller generating a warning sent to the indicator, or may be apparent simply in the reported data. For example, the data reporting at the indicator could be a trace over time (e.g., data points every 5 minutes), and the indication is simply a deviation of the line to higher values. Or, there could be a marker line in the indicator making deviations above the line more apparent. Or, if the indicator is a display screen, the controller could direct the screen to flash the data points that are above the standard.

Argon-36 Embodiment

The embodiment described above has as an important use argon of diminished radioactivity for use in detectors, including dark matter detectors. The method uses the clear detectable distinction between $^{36}$Ar and $^{40}$Ar. As it happens, $^{36}$Ar has a sufficient physics distinction from the primary radioactive species, $^{39}$Ar, to allow it to be purified from $^{39}$Ar (and, as a result of the physics, from $^{40}$Ar). To the degree that the separation process may not exclude $^{38}$Ar as effectively as it excludes $^{39}$Ar, no harm is done as this is a non-radioactive species of chemical equivalence.

Disclosed is the use of low-radioactivity argon for radiation detectors. There is a growing demand for low radioactivity argon, particularly for radiation detectors. Argon gas is generally collected from the atmosphere; however, this argon contains a small amount of Argon-39 and is therefore very slightly radioactive. Currently, the only source for low radioactivity argon is argon that is collected for underground sources where the primary isotope is Argon-40, and there is little to no Argon-39.

By using known, proven techniques it is possible to separate the isotopes of argon taken from the atmosphere. For low-level radiation detectors, the focus has been on separating the Argon-40 and Argon-39 in atmospheric argon. Generally, it is easiest to separate isotopes that have greater mass differences. Although Argon-40 is the most abundant argon isotope in the atmosphere and, therefore, may seem like the obvious isotope to enrich, the mass difference between Argon-36 and Argon-39 is greater than the difference between Argon-40 and Argon-39. Through isotope separation techniques, one can obtain low radioactivity argon that is mostly Argon-36, and this can then be used as an alternative to underground argon in radiation detectors requiring low radioactivity argon.

Disclosed is the use of the isotope Argon-36 as low-radioactivity argon free of the isotope Argon-39, and, more particularly, the use of Argon-36 as a competitive source of low radioactivity argon for radiation detectors. Currently, underground argon appears to be the sole source of low-radioactivity argon. However, disclosed herein is that instead the consumers of low-radioactivity underground argon could use isotopically pure Argon-36, or isotopically enriched Argon-36 (still having residual Argon-40, Argon-38, and therefore highly reduced Argon-39), as a substitute for low-radioactivity underground argon.

While demand for low radioactivity argon for use in sensitive radiation detectors is in part owing to use for large dark matter search experiments, low-radioactivity argon is also used in radiation detectors for National Security and as a calibration gas for radiation detectors used for radiometric dating techniques. Currently the only source for argon that is low in the isotope Argon-39 is from an underground source. The disclosed approach provides an alternative source for low radioactivity argon.

Low radioactivity argon can only be had in 2 ways, either mined from the underground where the concentration of Argon-39 is lower than in the atmosphere, or through separating the argon isotopes in the atmosphere to remove the radioactive Argon-39. There are already uses for low-radioactivity argon, and the source of this argon is from the underground. Disclosed herein is the use of enriched Argon-36 in radiation detectors.

Separating isotopes of argon is a standard technique. One of the earliest publications on argon isotope enrichment by thermal diffusion is from 1950 (Zucker et al., Physical Review, v80, no. 6, p. 966 et seq., Dec. 15, 1950). Additionally, Argon-36 is available from the National Isotope Development Center (isotopcs.gov). Additionally, commercial sources for >99% pure Argon-36 include Sigma Aldrich (Product #601764 ALDRICH; St. Louis, Mo.); National Isotope Development Center at Oak Ridge National Laboratory (TN); Cambridge Isotope Laboratories, Inc. (Tewksbury, Mass.); and Trace Sciences International Corp. (Wilmington, Del.). There are also new enrichment techniques (thermoacoustic) being used for Neon-20/Neon-22 separation, which can be used for argon. Geller et al., J. Acoust. Soc. Am. 115 (5), Pt. 1, pp. 2059-70, May 2004.

The need for low radioactivity argon in dark matter and other radiation detectors is discussed in the scientific literature. For example, H. Babcock et al. Technical Report, Princeton University, 2008 ("First Large Scale Production of Argon Depleted in $^{39}$Ar from Underground Wells"), The currently disclosed approach is to use Argon-36 rather than Argon-40, because, although less abundant in the atmosphere, it is easier to separate from Argon-39 (and Argon-40), than it is to separate Argon-40 from Argon-39.

The disclosed approach of using Argon-36 can be used, inter alia, to provide the low radioactivity argon for the Darkside Darkmatter detector, National Security detectors at Pacific Northwest National Lab, and as calibration gas for the detector used for radiometric dating detectors in Europe, and could be used for radiation detectors at airports and border crossings.

Below are examples of consumers of low radioactivity underground argon who could us the disclosed approach of using Argon-36 instead:

(A) Dark matter search experiments using argon require large masses of argon, on the order of many kilograms, and in the future many tons. These detectors are very sensitive to naturally occurring radioactivity, which limits their effectiveness at searching for Dark Matter. Although it is possible to purify argon to a high level with contamination concentrations lower than 1 part per trillion, including any naturally occurring radioactivity, the intrinsic radioactive Argon-39 in argon derived from the atmosphere is the irreducible background for these detectors. The Darkside and DEAP experiments are both using liquefied argon as a target for Dark Matter particles, which will produce a light pulse (scintillation light) when Dark Matter interacts in the liquid argon. Besides the low Argon-39 content, there is nothing special about the underground argon and, therefore, these detectors can use Argon-36 instead. See, darkside.lngs.infn.it/ds-50; and deap.phy.queensu.ca (B) The radioactive isotope Argon-37 is an isotope of interest for Comprehensive Nuclear Test Ban Treaty compliance to check for underground nuclear weapons testing. The proportional counters used to search for Argon-37 are also limited by the background produced from the Argon-39 contained in atmospheric argon; like the Dark Matter detectors. Underground argon has been supplied to the group making these proportional counters for Argon-37 counting. This is a consumer that needs a constant supply of Argon-39 free argon, which is currently being supplied by the Underground Argon program of the Darkside Dark Matter search, and could use the disclosed Argon-36 instead. It is understood that an argon sample from the field is mixed with low-radioactivity argon and a quenching gas (methane), and then loaded into the proportional counters. The counter is then allowed to search for Argon-37 decays over a period of time. See, www.ctbto.org/fileadmin/user_upload/ISS_2009/Poster/OSI-24B%20%28US%29%20-%20Craig_Aalseth%20etal.pdf; and Measurement of 37Ar to support technology for On-site Inspection under the Comprehensive Nuclear-Test-Ban Treaty, C. E. Aalseth, et al., arxiv.org/ftp/arxiv/papers/1008/1008.0691.pdf.

(C) Calibration gas for radiometric dating: The Atom Trap Trace Analysis (ATTA) technique uses laser traps for counting individual Argon-39 atoms in an argon sample for radiometric dating. This technique is currently being used to determine the age of ground water. Since they are directly searching for the Argon- 39 concentration in an argon sample, to understand the lower limits of the ATTA counting technique a sample of argon that is free of Argon-39 is required for calibration. The Argon-39 free gas is input into the ATTA apparatus rather than an argon sample, and then the ATTA searches for Argon-39, which is of course not there. From this measurement, the lower limit on Argon-39 counting can be determined.

(D) The Heidelberg ATTA group has also been supplied with underground argon from the Darkside Dark Matter search, but similar to the National Security proportional counters, the ATTA apparatus could also use the disclosed Argon-36 rather than underground argon for this calibration program. The ATTA groups will also require a constant supply of low radioactivity argon and is directly tied to the Dark Matter programs. See, journals.aps.org/prl/abstract/10.1103/PhysRevLett.106.103001; and www.kip.uniheidelberg.de/matterwaveoptics/research/atta.

In embodiments, a purification of Argon-36 is conducted on argon obtained from underground sources. As such, the Argon-36 can have levels of Argon-39 that are for example about 1000-fold or more reduced over the levels in atmospheric argon, or about 1500-fold or more reduced. With this source material, the degree of purification can be less exacting. For example, a 3-fold purification of Argon-36 vs. Argon-40 will be expected to provide a significant purification vs. Argon-39. Thus, in embodiments, the purification provides an about 3-fold or better, or 5-fold or better, or 10-fold or better purification vs. Argon-40.

All ranges recited herein include ranges therebetween, and can be inclusive or exclusive of the endpoints. Optional included ranges are from integer values therebetween (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4 or more, or 3.1 or more. If there are two ranges mentioned, such as about 1 to 10 and about 2 to 5, those of skill will recognize that the implied ranges of 1 to 5 and 2 to 10 are within embodiments consistent with the invention.

Where a sentence states that its subject is found in embodiments, or in certain embodiments, or in the like, it is applicable to any embodiment in which the subject matter can be logically applied.

Embodiments consistent with the present invention described herein are of a quality control method with respect to argon, to using $^{36}$Ar, methods of forming the same, and the like. Although some embodiments have been discussed above, other implementations and applications are also within the scope of the following claims. Although embodiments of the invention herein have been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of embodiments of the present invention as defined by the following claims.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

What is claimed is:

1. A method of conducting on-site quality control during production of underground argon, comprising:
concurrent with extraction of underground argon material, periodically sampling the argon material;
measuring an index amount of at least one of (a) an $^{36}$Ar to $^{40}$Ar ratio or (b) an $^{38}$Ar to $^{40}$Ar ratio from the sampled argon material; and
conducting one or more of the following:
interrupting production to determine a source of infiltration when a measured index amount for a sample indicates an infiltration of atmospheric argon that is outside a production quality standard, or
cataloging whether a production run satisfies a product quality standard for lack of atmospheric argon based on the measured index amounts for the samples when a production run for the argon, having a production run size, is complete.

2. The method of claim 1, wherein the measuring is conducted with sufficient sampling and immediacy of timing such that any infiltration of atmospheric argon is stopped prior to being sufficient to put a production run at risk of not meeting the product quality standard, and wherein the production is conducted until a production run meeting the product quality standard is achieved.

3. The method of claim 2, wherein the index amount is the $^{36}$Ar to $^{40}$Ar ratio.

4. The method of claim 2, wherein the production is configured to provide a reservoir, sized at a fraction of the size of a production run, of nominally purified argon that will be diverted if the measured index amount so indicates.

5. The method of claim 4, wherein the index amount is the $^{36}$Ar to $^{40}$Ar ratio.

6. The method of claim 1, wherein two or more product quality standards based on the index amount exist, each signifying a different level of purity from atmospheric argon, and wherein cataloging is to the highest standard applicable, assuming any are applicable.

7. The method of claim 6, wherein the index amount is an $^{36}$Ar to $^{40}$Ar ratio.

8. The method of claim 1, further comprising:
conducting multiple pilot argon production runs from an underground source;
determining the index amounts for the argon of the production runs; and
determining, based on results of the determining steps, the production quality standard.

9. The method of claim 8, wherein the index amount is an $^{36}$Ar to $^{40}$Ar ratio.

10. The method of claim 1, wherein the sampling and measuring are conducted in real time.

11. The method of claim 1, wherein the interrupting production step is conducted.

12. The method of claim 1, wherein the cataloging step is conducted.

13. The method of claim 1, wherein the measuring is done with a system for determining whether underground-sourced argon is sufficiently free of atmospheric argon comprising:
an analyzer configured to provide data sufficient to determine an index amount, wherein the index amount is one of (a) an $^{36}$Ar concentration or an $^{36}$Ar to $^{40}$Ar ratio or (b) an $^{38}$Ar concentration or an $^{38}$Ar to $^{40}$Ar ratio;
an processor programmed to determine the determine the index amount from the data; and
an indicator that receives from the processor a signal sufficient for the indicator to indicate whether the index amount meets a quality standard.

14. A method of conducting quality control on a container of underground argon, comprising:
measuring for the argon an index amount, which is (a) an $^{36}$Ar to $^{40}$Ar ratio or (b) an $^{38}$Ar to $^{40}$Ar ratio; and
cataloging whether the argon satisfies a product quality standard for lack of atmospheric argon based on the measured index amount.

15. The method of claim 14, further comprising returning the container of underground argon to a supplier if the argon does not satisfy the product quality standard.

16. A system for determining whether underground-sourced argon is sufficiently free of atmospheric argon comprising:
an analyzer configured to provide data sufficient to determine an index amount, wherein the index amount is one of (a) an $^{36}$Ar concentration or an $^{36}$Ar to $^{40}$Ar ratio or (b) an $^{38}$Ar concentration or an $^{38}$Ar to $^{40}$Ar ratio;
an processor programmed to determine the determine the index amount from the data; and
an indicator that receives from the processor a signal sufficient for the indicator to indicate whether the index amount meets a quality standard.

17. The system of claim 16, wherein the index amount is an $^{36}$Ar concentration or an $^{36}$Ar to $^{40}$Ar ratio.

18. The system of claim 16, wherein the analyzer is connected to an argon production system that processes underground argon material such that material is automatically periodically sampled and analyzed by the analyzer, and such that the indicator periodically provides the indication.

19. The system of claim 18, wherein the index amount is an $^{36}$Ar concentration or an $^{36}$Ar to $^{40}$Ar ratio.

20. The system of claim 18, wherein the system is configured such that the analyzer and processor are operated with sufficient sampling and immediacy of timing such that any infiltration of atmospheric argon can be stopped prior to being sufficient to put a production run at risk of not meeting a product quality standard, and wherein the production is conducted until a production run meeting the product quality standard is achieved.

* * * * *